United States Patent [19]

Nijkerk et al.

[11] Patent Number: 5,320,095
[45] Date of Patent: Jun. 14, 1994

[54] DEVICE FOR USE WITH THE INHALATION OF POWDERED MATERIALS CONTAINED IN ROD-SHAPED CAPSULES

[75] Inventors: Alfred J. Nijkerk, Amsterdam; Jarig E. Schram, Amstelveen; Sander J. Sinot, Amsterdam, all of Netherlands

[73] Assignee: Pharmachemie B.V., Ga Haarlem, Netherlands

[21] Appl. No.: 924,020

[22] PCT Filed: Dec. 10, 1991

[86] PCT No.: PCT/NL91/00259

§ 371 Date: Sep. 23, 1992

§ 102(e) Date: Sep. 23, 1992

[87] PCT Pub. No.: WO92/10230

PCT Pub. Date: Jun. 25, 1992

[30] Foreign Application Priority Data

Dec. 10, 1990 [NL] Netherlands .................. 9002706

[51] Int. Cl.⁵ ............................................. A61M 15/00
[52] U.S. Cl. ............................. 128/203.15; 128/203.23
[58] Field of Search ................. 128/203.15, 203.23, 128/203.21, 203.12; 222/88; 604/58

[56] References Cited

U.S. PATENT DOCUMENTS

| 2,517,482 | 8/1950 | Hall | 128/203.15 |
| 3,918,451 | 11/1975 | Steil | 128/203.15 |
| 3,991,761 | 11/1976 | Cocozza | 128/203.15 |
| 4,116,195 | 9/1978 | James | 604/244 |
| 4,627,432 | 12/1986 | Newell | 128/203.15 |
| 4,884,565 | 12/1989 | Cocozza | 128/203.21 |

FOREIGN PATENT DOCUMENTS

| 0005585 | 11/1979 | European Pat. Off. . | |
| 0041783 | 12/1981 | European Pat. Off. | 128/203.15 |
| 2704574 | 8/1977 | Fed. Rep. of Germany . | |
| 2264563 | 10/1975 | France . | |
| 2061735 | 5/1981 | United Kingdom | 128/203.15 |
| 2178965 | 2/1987 | United Kingdom | 128/203.15 |
| 8907464 | 8/1989 | World Int. Prop. O. . | |

*Primary Examiner*—Edgar S. Burr
*Assistant Examiner*—Eric P. Raciti
*Attorney, Agent, or Firm*—Browdy and Neimark

[57] ABSTRACT

The invention relates to a device for use with the inhalation of powdered materials contained in rod-shaped capsules, having two parts (2, 3) which may be pivoted one relative to the other, and provided with a mixing chamber (7) having substantially tangentially directed air inlet openings, said mixing chamber having one end in communication with a mouth piece (6) and the other end in communication with a capsule receiving cavity (26), the latter being formed in conformity with the longitudinal sectional shape of a capsule and having at at least one longitudinal end a passage opening (27) for a transversely (=in the longitudinal direction of the capsule receiving cavity) reciprocating piercing needle, and wherein the part (2) of the device comprising the mouth piece (6) is mounted to pivot relative to the capsule receiving cavity comprising part (3) of the device between a closed ready for use-position and an opened position permitting the insertion of a capsule. In accordance with the invention the mouth piece (6) is integrally formed with the mixing chamber (7), whereas the capsule receiving cavity (26) is provided in a bottom section (25) which closes the mixing chamber (7) in the closed or ready for use-position and is making part of said other part (3) of the device.

7 Claims, 3 Drawing Sheets

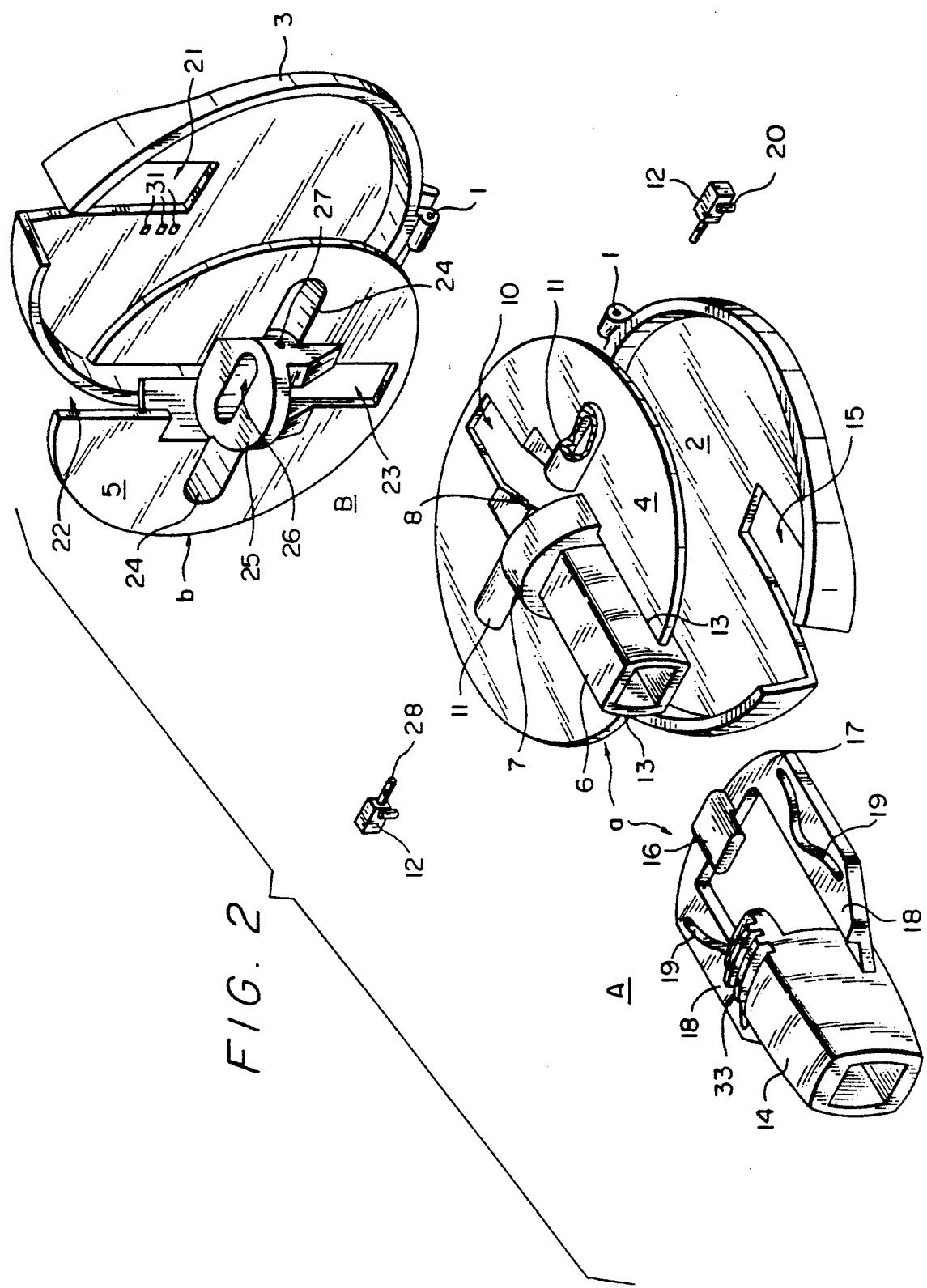

DEVICE FOR USE WITH THE INHALATION OF POWDERED MATERIALS CONTAINED IN ROD-SHAPED CAPSULES

FIELD OF INVENTION

The invention relates to a device for use with the inhalation of powdered materials contained in rod-shaped capsules, of the type, comprising a mixing chamber having substantially tangentially directed air inlet openings, said mixing chamber having one end in communication with a mouth piece and the other end in communication with a capsule receiving cavity, the latter being formed in conformity with the longitudinal sectional shape of a capsule and having at least one longitudinal end a passage opening for a transversely (=in the longitudinal direction of the capsule receiving cavity) reciprocating piercing needle, and wherein the part of the device comprising the mouth piece is mounted to turn relative to the capsule receiving cavity comprising part of the device between a closed ready for use-position and an opened position permitting the insertion of a capsule.

BACKGROUND

Such devices are already known in various embodiments. A typical example of such a well-known device is disclosed in NL-A-176837 and NL-A-179345.

With this well-known device the mouth piece comprising part of the device is rotatably mounted—about an axis that is positioned excentrically to its longitudinal axis—relative to the other part of the device, which comprises the mixing chamber, the capsule-receiving cavity and the piercing needle(s).

The insertion of a capsule in the receiving cavity is rather difficult, because this is to take place via the end of the mixing chamber facing the mouth piece. The removal of an emptied capsule may also be difficult.

Another typical example of a well-known device of the type above referred to is disclosed in EP-A-0041783. With this well-known device the mouth piece forms a part which may be removed from the rest of the device, so that the device may be loaded with a fresh capsule and an emptied capsule may be removed therefrom by taking the mouth piece off. Moreover there are provisions with this well-known device to jammingly hold a capsule within the receiving cavity. For this purpose the walls of the capsule receiving cavity are provided with ribs. The piercing of the capsule is effected automatically when the device is closed by placing the mouth piece, whereby the mouth piece actuates the piercing needle(s) and moreover—upon retraction of the piercing needle(s)—actuates an ejecting member. This means that when the device is closed upon placing a capsule, the latter will be automatically pierced and then, for direct use, ejected into the mixing chamber. Thus the closed position is also the use-position. Consequently it is not possible to place a capsule for later use i.e. to postpone piercing of the capsule until the moment at which the device is actually used.

SUMMARY OF THE INVENTION

The invention aims at providing an improved device of the type under consideration.

In accordance with one aspect of the invention an inhalation device of the type defined in the first part of claim 1 and disclosed in NL-A-176837 (vide also NL-A-179345) is provided, which is characterized in that the mouth piece is integrally formed with the mixing chamber, whereas the capsule receiving cavity is provided in a bottom section which closes the mixing chamber in the closed or ready for use-position and is made part of said other part of the device. As a result of this the accessibility of the receiving cavity has been improved, so that a capsule can now be easily put into its seat. Moreover cleaning has become easier.

In accordance with a second aspect of the invention an inhalation device of the type defined in the first part of claim 2 and disclosed in EP-A-0041783 is provided, which is characterized in that the mouth piece consists of two sections, one of which forms part of one of the movably connected body parts and the other of which is mounted for a sliding movement relative to said first section between a retracted, inactive position and an extended active position, wherein the second mouth piece section carries the piercing needle(s) and the ejecting member, whereas the body part containing the capsule-receiving cavity is mounted such that it can be moved into its closed position and from the latter position in the opened position only when the mouth piece takes its retracted position.

In this embodiment, when the mouth piece is in its retracted position, it is possible to place a capsule into the receiving cavity for later use and then close the device without the capsule being pierced. The piercing will be effected only when the user actually wishes to use the device. For that purpose the user will have to extend the mouth piece so as to be able to take it into his mouth, thereby automatically effecting the piercing of the capsule and the ejection of the latter into the swirl chamber. Furthermore it can not occur that an inhalation attempt is made with a non-pierced capsule within the swirl chamber, such as e.g. with the device according to NL-A-176837.

In accordance with a further feature of the invention the two parts of (the body of) the device are connected about an axis that is located in a center plane of the mouth piece on that side of the mixing chamber that is turned away from the free mouth piece end, and directed perpendicularly to the longitudinal axis of the mouth piece.

Due to this the device of the invention has in principle obtained the character of an easily openable and closable box. The manner of using the inhalation device of the invention has thus become more simple, and is now of a rather "natural" character.

BRIEF DESCRIPTION OF DRAWING

The invention will be hereinafter further explained by way of example with reference to the drawing.

FIG. 2 is a view as shown in FIG. 1, but with the composing parts in a deassembled state;

DETAILED DESCRIPTION OF EMBODIMENT(S)

Figure 1:
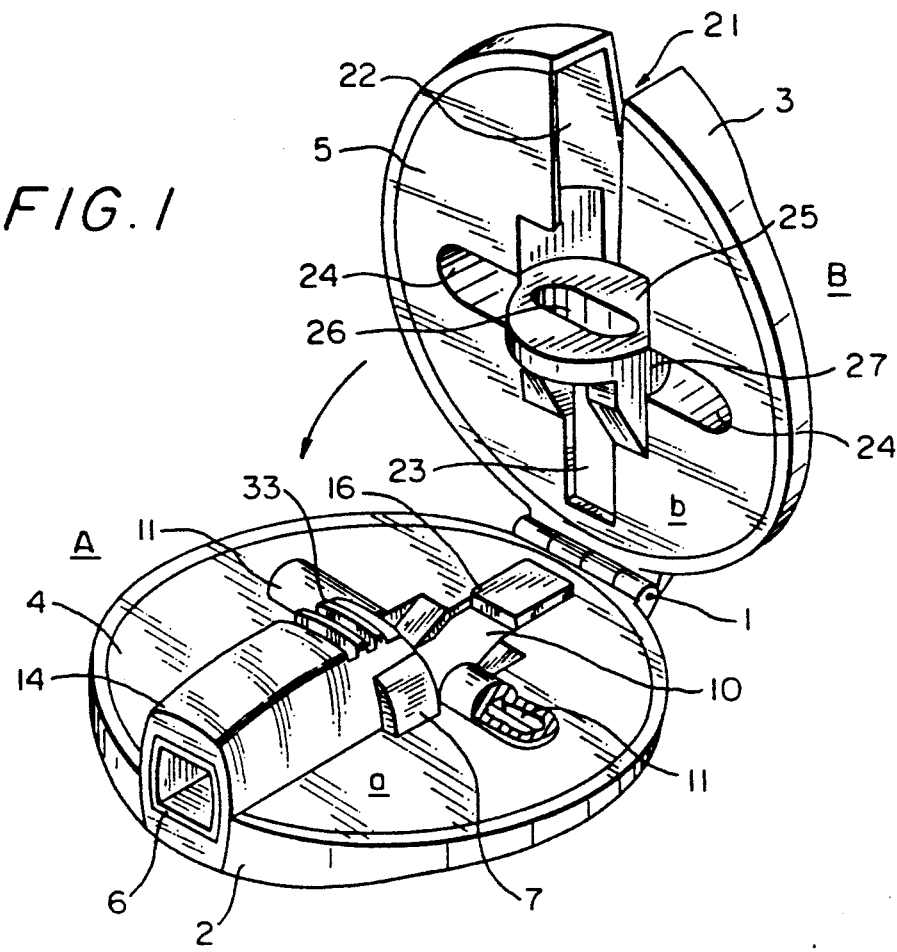
FIG. 1 is a perspective view of the inhalation device according to the invention, in the opened position and with the mouth piece in its retracted position.

The inhalation device shown in the drawings comprises two parts A and B, which are pivotally connected about an axis 1. These two parts may be closed in the arrow direction from the opened position shown in FIG. 1 to form a relatively flat box.

The parts A and B each comprise a circular shell 2 and 3 respectively, containing a filling a and b respectively.

The two fillings a and b, which together constitute the proper inhalation device, will be hereinafter further described with reference to the further figures of the drawings.

The filling a is formed by a circular support plate 4, which is integrally formed with a mouth piece section 6 and a substantially flat-cylindrical mixing and swirl chamber 7 connected with the latter; in the assembled position, the support plate 4 just fits within the circumferential edge of the shell 2.

The axis of the mouth piece section 6 and the chamber 7 connected therewith coincides with a center line lying in the upper surface of the support plate 4 and directed at right angles to the pivot axis 1, whereas the terminal edge 8 of the chamber 7, turned away from the upper portion of the mouth piece section 6, is located in a plane which passes through the centre of the support plate and is directed at right angles to said center line.

The terminal edge 8 has a portion which is located under the support plate 4 and is extended towards the pivot axis 1 to form an arcuate support means 8a (vide FIG. 3) for a bottom section which has still to be described and comprises part of the filling b of the part B.

Figure 5:
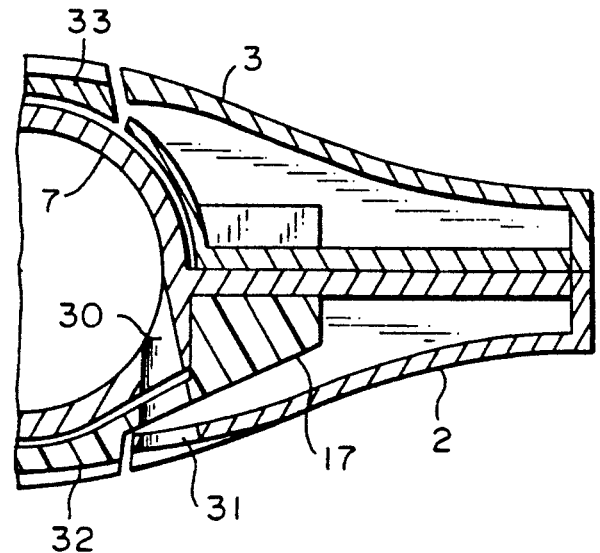
FIG. 5 is a cross-section along the line V—V in FIG. 3.
Figure 7:
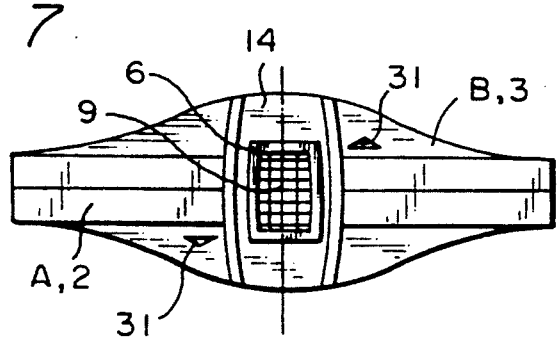
FIG. 7 is a front view on true scale of the inhalation device in its closed position.

A perforated partition 9 is provided between the mouth piece section 6 and the chamber 7. At two diametrically opposed locations of the circumferential wall of the chamber 7 substantially tangentially directed air inlet passages 30 are provided, which align with air inlet openings 31 provided in the shells 2 and 3 (vide FIGS. 5, 2 and 7).

Behind the chamber 7 the support plate 4 is recessed at 10 up to adjacent the circumferential edge of the plate. Guide ways 11 extend at right angles from the two longitudinal edges of the recess 10 and are adapted to receive block-shaped needle carriers 12 (vide FIG. 2) and to guidingly retain these carriers in the transverse direction. The guide ways 11 are formed by upwardly directed bulgings of the support plate 4.

On the inner mouth piece section 6 which is fixedly connected to the support plate 4, there is provided an outer mouth piece section 14, which may slide on the mouth piece section 6 between a retracted position (FIGS. 1 and 3) and an extended or active position. For this purpose a slot 13 is cut in the support plate 4 on both sides of the fixed mouth piece section 6, while the outer mouth piece section 14 projects with its lower portion through a corresponding recess 15 of the shell 2. The outer mouth piece section is provided with rearwardly extending lower and upper finger grip tongues 32 and 33 respectively (FIGS. 3 and 5), which abut—in the retracted position of the mouth piece section 24—against the cross edge of the recess 15 in the shell 2 and against the cross edge of a similar, still to be described recess in the shell 3 (FIG. 3) respectively. In the retracted position the outer terminal edges of the inner and outer mouth piece sections 6 and 14 lie in a common plane within the outer circumference of the shell 2.

An ejecting tongue 16 is connected with the outer mouth piece section 14 (vide FIG. 2) which is located within the rearward part of the recess 10 (adjacent the pivot axis 1) of the support plate 4 when the mouth piece is in its retracted position and which will be moved through the slot 10 forwardly when the outer mouth piece section is moved into its extended position. The ejecting tongue 16 is connected to the outer mouth piece section 14 by means of a connecting yoke 17 (vide FIG. 2) which, in the assembled state of the device, is located under the support plate 4 and for this reason is provided slightly under the horizontal center plane of the mouth piece section 14. When formed of plastics material the connecting yoke 17 may resiliently bend relative to the mouth piece section 14 in a sufficient degree to enable it to be assembled with the support plate 4.

As shown in FIG. 2, guide grooves 19, which function like cam guides, are provided in the upper surfaces of the legs 18 of the connecting yoke and guide pins 20 which project from the lower side of the needle carriers 20 are engaged within these grooves.

The filling b of the part B comprises a substantially circular support plate 5 which—in the assembled state—just fits within the circumferential edge of the shell 3 and which is provided with a slot 22 which corresponds with the slot 21 in the shell 3 to accommodate the upper portion of the outer mouth piece section 14 that projects upwardly from the support plate 4 of the part A. The support plate 5 is also provided with a slot 23 which aligns with the slot 10 in the support plate 4, and with recesses 24 for accommodating the bulgings of the support plate 4 which constitute the guideways 11 for the needle carriers.

Figure 3:
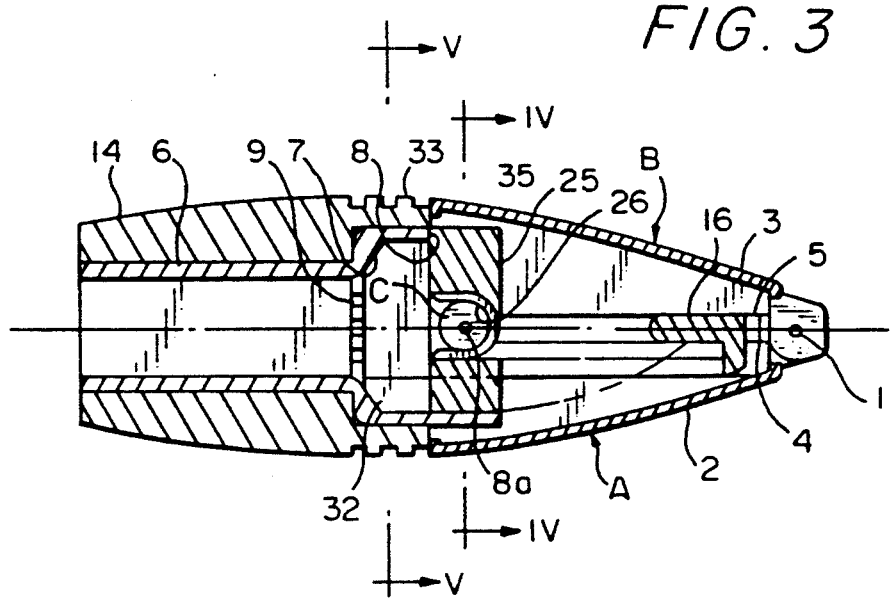
FIG. 3 is a cross-sectional view of the device in the closed position, along the vertical midplane.

The support plate 5 is integrally formed with a bottom section 25 serving to close the rear side of the mixing chamber 7 in part A when the device is in its closed position as shown in FIG. 3. The bottom section 25 has an end face that is turned away from the pivot axis 1 and engages the terminal edge 8 of the chamber 7. This end face forms a part of a cylindrical surface about the pivot axis 1. Furthermore—in the closed position of the device—the bottom section 25 engages the rearwardly extending supporting portion 8a of the mixing and swirl chamber 7. A cavity 26 is provided in said end face of the bottom section 25, which cavity is shaped to conform to the longitudinal section of a rod-shaped capsule having rounded ends. On the wall of the cavity 26 pressure points are formed by ribs 35 (FIGS. 3 and 4) which extend in the capsule-inserting direction and provide for a slightly jamming seat for the capsule C in the cavity 26. The longitudinal axis of the cavity 26 extends diametrically relative to the bottom section 25 and parallel to the pivot axis 1. In the closed position of the device this longitudinal axis coincides with the common axis of the piercing needles carried by the blocks 12 in the guideways 11. Passage openings 27 (see FIG. 4) for the piercing needles 28 are provided in the spherical end walls of the cavity 26 and positioned on said longitudinal axis. As seen in the rearward direction the cavity 26 merges into a passage slot 40 for the ejecting tongue 16 described hereinabove.

Figure 4:
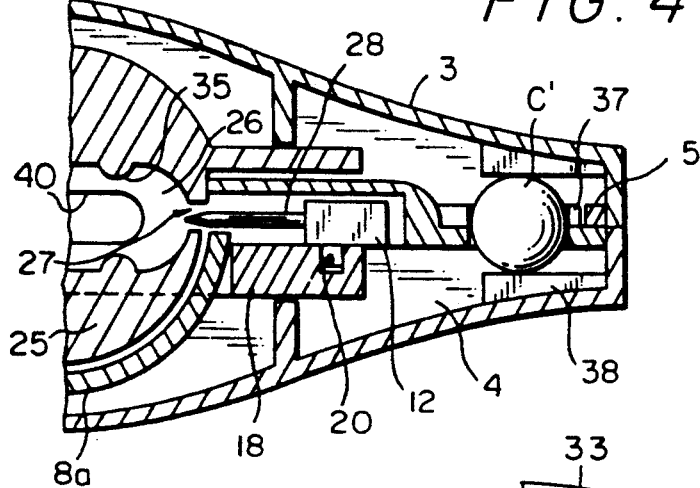
FIG. 4 is a cross-section along the line IV—IV in FIG. 3.
Figure 6:
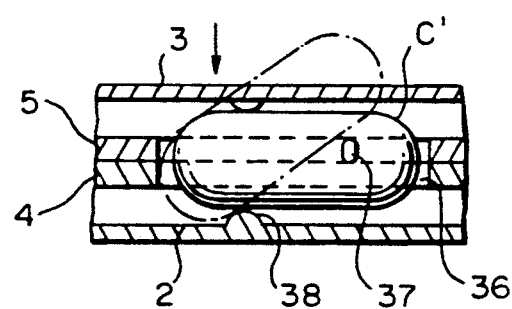
FIG. 6 is a cross-sectional view of a detail.

The device described hereinabove is also adapted to contain a supply of capsules. For this purpose in principle all that space within the closed shells 2 and 3, which has not yet been taken by the mouth piece sections, the mixing chamber, the bottom section and the needle carriers, is available for capsule storage. In those zones of the superimposed support plates 4 and 5 which are not covered by the latter parts, recesses may be provided, the form of which corresponds with the longitudinal sectional shape of the capsules. A respective detail is shown in FIG. 4, where a supply capsule C' is received in a broad-dimensioned recess 36 of the support plate 4 and held jammed therein by ribs 37 projecting from the edges of said recess. The capsule is supported on a cross rib 38 provided on the inner side of the shell 2, which rib may—after the part B being opened—act as a tilting rib and thus facilitate the removal of the capsule (vide FIG. 6).

The preferred inhalation device shown in the drawings forms—in its closed and retracted position—a rather compact and flat article, the size of which hardly goes beyond that of a classic pocket watch or powder compact, so that it may be put away in the user's clothing in a comfortable manner. The actions to be performed for using the device hardly require instructions. The opening of the "box" and the insertion of a capsule may be considered as natural actions and the same applies for the act of taking the finger grip tongues 32 and 33 between thumb and index finger to extend the mouth piece so as to take the latter into the user's mouth.

When extending the mouth piece, the capsule ends are automatically pierced. With reference to FIG. 2 it will be understood that substantially halfway of the extension movement—when the guide pins 20 of the needle carriers 12 will be positioned in the inwardly directed curves of the guideways 19—the needles 28 are completely inserted and that these needles will thereafter—when the extension movement is continued—be retracted from the capsule ends. In the final phase of the extension movement, when the needles have already been retracted from the capsule, the ejecting tongue 16 will pass through the passage slot 40 in the bottom section 25 to eject the pierced capsule from the bottom section 25 into the mixing chamber 7.

The rather flat shape facilitates the handling during inhaling, whereby the wall portions extending laterally from the extending mouth piece constitute an abutment surface for the user's lips and thus contribute to an optimal use.

For the rest the operation during inhaling corresponds to that of the well-known device. Air from the surrounding atmosphere is sucked through the tangential air inlet passages into the chamber 7 and causes the capsule to turn around within the chamber, whereby the powdered material is expelled from the capsule and is mixed with the air within the chamber 7, so that an air-powder mixture is breathed in by the user.

The device described hereinabove may be suitably formed of plastics material.

We claim:

1. In a device for facilitating the inhalation of powdered materials contained in rod-shaped capsules, said device comprising a mouthpiece, a capsule receiving cavity, a mixing chamber having substantially tangentially directed air inlet openings and having one end in communication with said mouthpiece and another end in communication with said capsule receiving cavity, a reciprocatively movable piercing needle for piercing a rod-shaped powder containing capsule within said cavity, means for reciprocating said piercing needle so as to pierce the powder containing capsule, and a housing having a first part containing said mouthpiece and a second part containing said capsule receiving cavity and wherein said first part and said second part are mounted together to turn relative to one another between a closed position for use and an opened position for insertion of a capsule, the improvement wherein said mouthpiece is integrally formed with said mixing chamber, said two parts of said housing are connected about a pivot axis extending substantially perpendicular to a longitudinal axis of said mouthpiece; means for reciprocatively moving said mouthpiece along said longitudinal axis between a first inactive position wherein said mouthpiece is closer to said pivot axis and a second active position wherein said mouthpiece is farther away from said pivot axis, and means for causing movement of said piercing needle to pierce the powder containing capsule upon movement of said mouthpiece from said first inactive position to said second active position.

2. A device according to claim 1, further comprising a tongue-shaped ejecting member and driving means for driving said ejecting member to move a pierced capsule from said capsule receiving cavity into said mixing chamber when said mouthpiece is moved from said first inactive position to said second active position and after movement of said piercing needle.

3. A device according to claim 2, wherein said mouthpiece comprises a slidable section carrying a U-shaped connecting piece having leg portions located on either side of said mixing chamber, and a bridge portion carrying said tongue-shaped ejecting member.

4. A device according to claim 3, wherein said first part of said housing and said second part of said housing form a shell-shaped box, each of said first part and said second part containing a support plate just fitting within a circumferential edge thereof, said support plates being adjacent one another when said housing is closed.

5. In a device for use with the inhalation of powdered materials contained in rod-shaped capsules, comprising a body with two parts mounted to be moved one relative to the other and provided with a mixing chamber having tangentially directed air inlet openings, said mixing chamber having one end in communication with a mouthpiece and an opposite end in communication with a capsule receiving cavity, said receiving cavity being generally complementary in shape to a rod-shaped capsule and being adapted to jammingly hold a capsule, at least one longitudinal end of said cavity having a passage opening for a transversally reciprocating piercing needle, an ejecting member movably mounted to be moved into the receiving cavity to urge a capsule from said cavity into the mixing chamber, said mouthpiece being mounted for movement relative to the capsule receiving cavity between a receiving cavity closed position and an opened position permitting the insertion of a capsule into said cavity, said mouthpiece being provided with means for activating said piercing needle and then for moving said ejecting member to said receiving cavity closed position when said mouthpiece is moved into an extended active position, the improvement wherein said mouthpiece consists of a first section forming a part of one of said two parts of said body, and another section of said mouthpiece being mounted for sliding movement relative to said first section between a retracted inactive position and said extended active position, said second section of said mouthpiece carrying said piercing needle and said ejecting member; another of said two parts of said body carrying said capsule receiving cavity and said two parts of said body comprising means for moving into the closed position of said body and then into the opened position of said body only when said mouthpiece is in said retracted inactive position.

6. A device according to claim 5, comprising needle control means to reciprocate said piercing needle from a non-piercing position when said mouthpiece is in the retracted inactive position to a capsule piercing position when said mouthpiece is in the extended active position.

7. A device according to claim 6 wherein said means comprises a slidable section of said mouthpiece carrying a U-shaped connecting piece with a leg portion located on either side of the mixing chamber and a bridge portion carrying said ejecting member, each said leg portion carrying guide means for cam-guiding driving means for said piercing needle.

* * * * *